United States Patent [19]

Gerlach et al.

[11] Patent Number: 5,441,736
[45] Date of Patent: Aug. 15, 1995

[54] ACTINOBACILLUS PLEUROPNEUMONIAE OUTER MEMBRANE LIPOPROTEIN A AND USES THEREOF

[75] Inventors: Gerald F. Gerlach; Philip J. Willson, both of Saskatoon, Canada; Amalia Rossi-Campos, Lincoln, Nebr.; Andrew A. Potter, Saskatoon, Canada

[73] Assignee: University of Saskatchewan, Saskatoon, Canada

[21] Appl. No.: 971,558

[22] Filed: Nov. 5, 1992

[51] Int. Cl.$^6$ .................... A61K 39/02; C07K 14/285
[52] U.S. Cl. ................ 424/190.1; 424/256.1; 424/825; 530/350; 530/395
[58] Field of Search ............. 424/88, 92, 190.1, 256.1, 424/825; 530/350, 359, 395; 435/69.3

[56] References Cited

PUBLICATIONS

Wood et al. (1985) Proc. Natl. Acad. Sci. 82, 1585–1588.
Gerlach et al. (1993) Infect. Immun. 61(2), 565–572.
Lathe (1985) J. Mol. Biol. 183, 1–12.
Thwarts et al. (1991) Infect. Immun. 59, 544–549.
Findlay. in Biological Membranes: A practical approach, Findlay et al, ed. IRL Press, Washington D.C., 1987, pp. 179–217.
Anderson, B. E., et al., *J. Bacteriol.* (1988) 170:4493–4500.
Bessler, W. G., et al., *J. Immunol.* (1985) 135:1900–1905.
Bessler, W., et al., *Z. Immun.* (1977) 153:11–22.
Bricker, T. M., et al., *Infect. Immun.* (1988) 56:295–301.
Deneer, H. G., and Potter, A. A., *Infect. Immun.* (1989) 57:798–804.
Hanson, M. S., and Hansen, E. J., *Mol. Microbiol.* (1991) 5:267–278.
Higgins, R., et al., *Can. Vet. J.* (1985) 26:86–89.
Hubbard, C. L., et al., *Infect. Immun.* (1991) 59:1521–1528.
MacInnes, J. I. and Rosendal, S., *Infect. Immun.* (1987) 55:1626–1634.
Melchers, F., et al., *J. Exp. Med.* (1975) 142:473–482.
Nelson, M. B., et al., *Infect. Immun.* (1988) 56:128–134.
Theisen, M., et al., *Infect. Immun.* (1992) 60:826–831.
Thirkell, D., et al., *Infect. Immun.* (1991) 59:781–784.

*Primary Examiner*—Charles L. Patterson, Jr.
*Assistant Examiner*—G. Bugaisky
*Attorney, Agent, or Firm*—Reed & Robins

[57] ABSTRACT

Novel vaccines for use against *Actinobacillus pleuropneumoniae* are disclosed. The vaccines contain at least one *Actinobacillus pleuropneumoniae* outer membrane lipoprotein A, or an immunogenic fragment thereof. Also disclosed are DNA sequences encoding these proteins, vectors including these sequences and host cells transformed with these vectors. The vaccines can be used to treat or prevent porcine respiratory infections.

14 Claims, 12 Drawing Sheets

```
  1  GATCGGCTTTACAGGCGATTGCAGAATGATTGAATTGTAAACTTTAGAGCT
     CTAGCCGAAAATGTCGCTAACGTCGTTACTAACTTAACATTTGAAATCTCGA

52  TTATATTTTGTTTAATGGTATTATATATATATTACTTATATATTTATGGTATTCTTAGTT
     AATATAAAAAACAAATTACCATAATATAAATGAATATAAATACTAAGAATCAA

103  TTTATTGTAAATTAAAGTGTTGTTTATTTTGTATTTAAGTATAAGGAATTT
     AATAACATTTAATTTCACAAATAAATAACATAAAATTCATATTCCTTAAA

154  TTTA ATG AAT ATT GCA ACA AAA TTA ATG GCT AGC TTA GTC GCT AGT GTA
     AAAT TAC TTA TAA CGT TGT TTT AAT TAC CGA TCG AAT CAG TCA CAT
          Met Asn Ile Ala Thr Lys Leu Met Ala Ser Leu Val Ala Ser Val>

203  GTG CTT ACC GCA TGT AGT GGC GGC TCA GGT TCA TCG TCT AAA CCA
     CAC GAA TGG CGT ACA TCA CCG AGT CCA AGT AGC AGA TTT GGT
     Val Leu Thr Ala Cys Ser Gly Gly Ser Gly Ser Ser Ser Lys Pro>

254  AAT TCG GAA CTT ACA CCT AAG GTT GAT ATG TCC GCA CCA AAA GCG GAG CAG
     TTA AGC CTT GAA TGT GGA TTC CAA CTA TAC AGG CGT GGT TTT CGC CTC GTC
     Asn Ser Glu Leu Thr Pro Lys Val Asp Met Ser Ala Pro Lys Ala Glu Gln>

305  CCA AAA AAA GAG GAA GTT CCA CAA GCG GAT AAT TCG AAA GCG GAA GAA CCA
     GGT TTT TTT CTC CTT CAA GGT GTT CGC CTA TTA AGC TTT CGC CTT CTT GGT
     Pro Lys Lys Glu Glu Val Pro Gln Ala Asp Asn Ser Lys Ala Glu Glu Pro>
```

FIG. 1A

```
356 AAA GAG ATG GCT CCG CAA GTA GAT AGC CCG AAA GCG GAA GAA CCA AAA AAT
    TTT CTC TAC CGA GGG GTT CAT CTA TCG GGC TTT CGC CTT CTT GGT TTT TTA
    Lys Glu Met Ala Pro Gln Val Asp Ser Pro Lys Ala Glu Glu Pro Lys Asn>

407 ATG GCT CCA CAA ATG GGT AAT CCA AAA CTA AAT GAC CCA CAA GTA ATG GCT
    TAC CGA GGT GTT TAC CCA TTA GGT TTT GAT TTA CTG GGT GTT CAT TAC CGA
    Met Ala Pro Gln Met Gly Asn Pro Lys Leu Asn Asp Pro Gln Val Met Ala>

458 CCG AAA ATG GAT AAT CCG CAA GTT CTA CGG GGT TTT CCT CTT CTT GAT TCA
    GGC TTT TAC CTA TTA GGC GTT TTT CTA CGG GGT TTT CCT CTT CTT GAT TCA
    Pro Lys Met Asp Asn Pro Gln Val Leu Arg Gly Phe Pro Leu Leu Asp Ser>

509 AAG GAT AAA AGT AAT GCG GAA ATT CTT AAG GAA TTA GGG GTT AAG GAT ATT
    TTC CTA TTT TCA TTA CGC CTT TAA GAA TTC CTT AAT CCC CAA TTC CTA TAA
    Lys Asp Lys Ser Asn Ala Glu Ile Leu Lys Glu Leu Gly Val Lys Asp Ile>

560 AAT TCA GGT ATC ATT AAT AAT GCT GAT GTA GTT CTG AAT TTA AAA ATA GAT
    TTA AGT CCA TAG TAA TTA TTA CGA CTA CAT CAA GAC TTA AAT TTT TAT CTA
    Asn Ser Gly Ile Ile Asn Asn Ala Asp Val Val Leu Asn Leu Lys Ile Asp>

611 GAA AAA GAT CAC ATT ACA GTC GTA TTA GAT AAG GGT AAG ATT AAT CGT AAT
    CTT TTT CTA GTG TAA TGT CAG CAT AAT CTA TTC CCA TTC TAA TTA GCA TTA
    Glu Lys Asp His Ile Thr Val Val Leu Asp Lys Gly Lys Ile Asn Arg Asn>
```

FIG. 1B

```
662  CAT CTA AAA GTA ACT AAT ACA ATT TCT GCT CAA GAC ATT AAA ACC TTA AAA
     GTA GAT TTT CAT TGA TTA TGT TAA AGA CGA GTT CTG TAA TTT TGG AAT TTT
     His Leu Lys Val Thr Asn Thr Ile Ser Ala Gln Asp Ile Lys Thr Leu Lys>

713  GAT TCT TCA GGC AAA TTG TTG GGT TAC TAT GGA TAT ATG CAG TTA AAT CAA
     CTA AGA AGT CCG TTT AAC CCA ATG ATA CCT ATA TAC GTC AAT TTA GTT
     Asp Ser Ser Gly Lys Leu Leu Gly Tyr Tyr Gly Tyr Met Gln Leu Asn Gln>

764  GTT CGA CAA GAT GAA AAT TAT AGC GAT CTA CTT TTT CAA TCA TTG AAT GAA TAT
     CAA GCT GTT CTA TTA ATA TCG GAT GAA AAA GTT AGT AGT TCA AAC TTA CTT ATA
     Val Arg Gln Asp Glu Asn Tyr Ser Asp Leu Leu Phe Gln Ser Leu Asn Glu Tyr>

815  TAT TTA TTA TCA ATG AAC GAT GCC AAA ATA CGT CCG ACT AAA TCT ATA
     ATA AAT AAT AGT TAC TTG CTA CGG CTA TAT GCA GGC TGA TTT AGA TAT
     Tyr Leu Leu Ser Met Asn Asp Ala Lys Ile Arg Pro Thr Lys Ser Ile>

866  TCA TAT AAG GGA GAC ATG TTT TAT AGT TAC AAA GAT GTA GGA AAT CAG AAA
     AGT ATA TTC CCT CTG TAC AAA ATA TCA ATG TTT CTA CAT CCT TTA GTC TTT
     Ser Tyr Lys Gly Asp Met Phe Tyr Ser Tyr Lys Asp Val Gly Asn Gln Lys>

917  TTA AAG GCT TCT GTA GAA GCT TCT TAT GAT GAT GTA ACA AAA AAA GTA TCA
     AAT TTC CGA AGA CAT CTT CGA AGA ATA CTA CAT TGT TTT TTT CAT AGT
     Leu Lys Ala Ser Val Glu Ala Ser Tyr Asp Asp Val Thr Lys Lys Val Ser>
```

FIG. 1C

```
 968 ATG AAA GTA TTT GGT GAG AAT AAT GAT TAC TGG AAA TTA GGT GAG TTT GGT
     TAC TTT CAT AAA CCA CTC TTA CTA ATG ACC TTT AAT CCA CTC AAA CCA
     Met Lys Val Phe Gly Glu Asn Asn Asp Tyr Trp Lys Leu Gly Glu Phe Gly〉

1019 AGA ACT AAT TTA TTA GAA AAT CAA GTG ACT GGA GCA AAA GTT GGC GAA GAT
     TCT TGA TTA AAT CTT TTA GTT CAC TGA CCT TTT CAA CCG CTT CTA
     Arg Thr Asn Leu Leu Glu Asn Gln Val Thr Gly Ala Lys Val Gly Glu Asp〉

1070 GGT ACC ATT ATA AAT GGA ACT TTA TAT TCT AAA ATA GAT AAT TTT CCT TTA
     CCA TGG TAA TAT TTA CCT TGA AAT ATA AGA TTT TAT CTA TTA AAA GGA AAT
     Gly Thr Ile Ile Asn Gly Thr Leu Tyr Ser Lys Ile Asp Asn Phe Pro Leu〉

1121 AAA CTA ACT CCT GAC GCA AAC TTC TCT GGG GGT ATT TTC GGT AAA AAT GCC
     TTT GAT TGA GGA CTG CGT TTG AAG AGA CCC CCA TAA AAG CCA TTT TTA CCG
     Lys Leu Thr Pro Asp Ala Asn Phe Ser Gly Gly Ile Phe Gly Lys Asn Gly〉

1172 GAA GTA TTA GCC GGA AGT GCT ATT AGT GAA AAA TGG CAA GGC GTA ATC GGT
     CTT CAT AAT CGG CCT TCA CGA TAA TCA CTT TTT ACC GTT CCG CAT TAG CCA
     Glu Val Leu Ala Gly Ser Ala Ile Ser Glu Lys Trp Gln Gly Val Ile Gly〉
```

FIG. 1D

1223 GCT ACG GCA ACC ACA AAA GAA GAT AAA AAA TAA ACGCTTTGCTAACTAAAC
     CGA TGC CGT TGG TGT TTT CTT CTA TTT TTT ATT TGCGAAACGATTGATTTG
     Ala Thr Ala Thr Lys Glu Asp Lys Lys Lys End>
                                                       a      a     >

1274 CAAAAGTTATCCTTCGGGATAGCTTTTTTACTTTTTAATCAGACCTAATAG
     GTTTTCAATAGGAAGCCCTATCGAAAAAATGAAAAAATTAGTCTGGATTATC

1325 TGCATCGGTAAAAGAT
     ACGTAGCCATTTTCTA

FIG. 1E

```
  1 TCTAGAAAATGCACTGACAAAATTAGGACTTTCAGTGCTGCCTATCATAG
    AGATCTTTTACGTGACTGTTTTAATCCTGAAAGTCACGACGGATAGTATC

52 GATTTTAAAAGTTTCCCGCACAATTGCCGATTTGGCGAACGAACCGAATAT
    CTAAAATTTCAAAGGGCGTGTTAACGGCTAAACCGCTTGCTTGGCTTATA

103 TCAACAAATCCATCTTGCCGAAGCGTTAGGTTATCGAGCGATGGATCGGCT
    AGTTGTTTAGGTAGAACGGCTTCGCAATCCAATAGCTCGCTACCTAGCCGA

154 TTTGCAGAGGTTGCAGAACGATTAAATTGTAAACTTTAGAGCTTTATATTT
    AAACGTCTCCAACGTCTTGCTAATTTAACATTTGAAATCTCGAAATATAAA

205 TGTTTGATGGTATTATATTATTTATGATTTTTTAGTTTTTATTGTAAATTAAAGT
    ACAAACTACCATAATATATAAATACTAAAAATCAAAAATAACATTTAATTTCA

256 GTTTATTTATTGTATTTAAGTATAAGGAATTTTTTA ATG AAT ATT GCA
    CAAATAAATAACATAAATTCATATTCCTTAAAAAAT TAC TTA TAA CGT
                                         Met Asn Ile Ala>

305 ACA AAA TTA ATA GCC GGT TTA GTC GCA GGT TTA GTG CTT ACC GCA TGT AGT
    TGT TTT AAT TAT CGG CCA AAT CAG CGT CCA AAT CAC GAA TGG CGT ACA TCA
    Thr Lys Leu Ile Ala Gly Leu Val Ala Gly Leu Val Leu Thr Ala Cys Ser>

356 GGC GGC GGC TCA TCG GGT TCA TCG CCT AAA CCA AAT TCG GAA TCT ACG CCT
    CCG CCG CCG AGT AGC CCA AGT AGC GGA TTT GGT TTA AGC CTT AGA TGC GGA
    Gly Gly Gly Ser Ser Gly Ser Ser Pro Lys Pro Asn Ser Glu Ser Thr Pro>
```

```
713 ATT TCC GAT ATT GAA TTG AAC CTT CAA TTA GAT AGC AAT GAT AAT GTG AAA
    TAA AGG CTA TAA CTT AAC TTG GAA GTT AAT CTA TCG TTA CTA TTA CAC TTT
    Ile Ser Asp Ile Glu Leu Asn Leu Gln Leu Asp Ser Asn Asp Asn Val Lys>
    _____a_____a_____

764 ATA TCT TTG TTA AAT GAG AAT TTA ATG CGT GAT AAT TTA ACG ATT AAT AAT
    TAT AGA AAC AAT TTA CTC TTA AAT TAC GCA CTA TTA AAT TGC TAA TTA TTA
    Ile Ser Leu Leu Asn Glu Asn Leu Met Arg Asp Asn Leu Thr Ile Asn Asn>
    _____a_____a_____

815 AAG ATT GCA GGT TCG GAT ATT AGA ACG TTA AAA GAT TCT TCA GGT AGA TTG
    TTC TAA CGT CCA AGC CTA TAA TCT TGC AAT TTT CTA AGA AGT CCA TCT AAC
    Lys Ile Ala Gly Ser Asp Ile Arg Thr Leu Lys Asp Ser Ser Gly Arg Leu>
    _____a_____a_____

866 TTA GGT TAT TAT GGT TAT GTG CAA GTT AAC TTA AAT CAA GTT ACA CAA CGT
    AAT CCA ATA ATA CCA ATA CAC GTT CAA TTG AAT TTA GTT CAA TGT GTT GCA
    Leu Gly Tyr Tyr Gly Tyr Val Gln Val Asn Leu Asn Gln Val Thr Gln Arg>
    _____a_____a_____

917 GAC CCA GAT AAT TAT AAG CAT CAG TTT GAA CTT TTA GTA ATA CAT TTA ATG
    CTG GGT CTA TTA ATA TTC GTA GTC AAA CTT GAA AAT CAT TAT GTA AAT TAC
    Asp Pro Asp Asn Tyr Lys His Gln Phe Glu Leu Leu Val Ile His Leu Met>
    _____a_____a_____

968 AAT GAT GCT GAG AAA ATA TTA CCA GAA AAG TCG TTA GAA TAT AAA GGT AGT
    TTA CTA CGA CTC TTT TAT AAT GGT CTT TTC AGC AAT CTT ATA TTT CCA TCA
    Asn Asp Ala Glu Lys Ile Leu Pro Glu Lys Ser Leu Glu Tyr Lys Gly Ser>
    _____a_____a_____
```

FIG. 2C

```
1019 ATG ATT TAC GGA TAT AAT ACT TCT GGA AAT GAA AAG CTT ACT GCA GAA GTC
     TAC TAA ATG CCT ATA TTA TGA AGA CCT TTA CTT TTC GAA TGA CGT CTT CAC
     Met Ile Tyr Gly Tyr Asn Thr Ser Gly Asn Glu Lys Leu Thr Ala Glu Val>

1070 AAT GCT AAA TAT GAT AGT TCA ACT AAA AAA TTA TCA ATG AAA GTA TAT GAT
     TTA CGA TTT ATA CTA TCA AGT TGA TTT TTT AAT AGT TAC TTT CAT ATA CTA
     Asn Ala Lys Tyr Asp Ser Ser Thr Lys Lys Leu Ser Met Lys Val Tyr Asp>

1121 AAT GAT CGT TAT TGG AAA TTA GGC GAA GTA ATG AGT AAC AAT GTT AGA TTA
     TTA CTA GCA ATA ACC TTT AAT CCG CTT CAT TAC TCA TTG TTA CAA TCT AAT
     Asn Asp Arg Tyr Trp Lys Leu Gly Glu Val Met Ser Asn Asn Val Arg Leu>

1172 CCA GAA GAA AAA GTT GAT GGT GTG AAA GTT CAA CTA AGA CCT TGT TAA AAT
     GGT CTT CTT TTT CAA CTA CCA CAC TTT GAT CTT GAT TCT AGA ACA ATT AAT
     Pro Glu Glu Lys Val Asp Gly Val Lys Val Gln Leu Arg Pro Cys *** Ile Asn>

1223 GCT CGT TTA TAT TTA AGC ACT TCG TGA CTT GGT AAT TTT AAT TGG GGA CTG CGG
     CGA GCA AAT ATA AAT TCG TGA CTT GAA CCA TTA AAA TTA ACC CCT GAC GCC
     Ala Arg Leu Tyr Leu Ser Thr Arg Glu Leu Pro Leu Lys Leu Thr Pro Asp Ala>

1274 AAT TTC TCC GGT ATT TTT GGG AAA AAC GGT GAA GTA CTG GCA GGA AAA
     TTA AAG AGG CCA TAA AAA CCC TTT TTG CCA CTT CAT GAC CGT CCT TTT
     Asn Phe Ser Gly Ile Phe Gly Lys Asn Gly Glu Val Leu Ala Gly Lys>
```

FIG. 2D

1325 GCG GAA AGC ATT AAG GGA GAA TGG CAA GGC GTA ATC GGT GCT ACG GCA ACA
     CGC CTT TCG TAA TTC CCT CTT ACC GTT CCG CAT TAG CCA CGA TGC CGT TGT
     Ala Glu Ser Ile Lys Gly Glu Trp Gln Gly Val Ile Gly Ala Thr Ala Thr⟩

1376 ACA AAA GAA GAT AAA AAA TAA CGCTTTGCTTACCAAACTAAAGCTATCCT
     TGT TTT CTT CTA TTT TTT ATT GCGAAACGAATGGTTTGATTTTCGATAGGA
     Thr Lys Glu Asp Lys Lys End⟩

1427 TCGGGATAGCTTTTTTACTTTTTAATCAGTGCCAATAGTGCATCGGTAAAA
     AGCCCTATCGAAAAAATGAAAAAATTAGTCACGGTTATCACGTAGCCATTTT

1478 GATTCCGGGTTTCATAATGTGCGTTATGTCCGGCATTAGGAATAAGCTGA
     CTAAGGCCCAAAGTATTACACGCAATACAGGCCGTAATCCTTATTCGACT

1529 TGATGAAGTTATTATCGGAGACGATTTTCTAAATTTCCGATCATATTCG
     ACTACTTCAATAATAATAGCCCTCTGCTAAAAAGATTTAAAGGCTAGTATAAGC

1580 CCGATCAAAAAGTGATAGTCTGCCGAGCTTCGGAGAGCTGCGGTAAAAAA
     GGCTAGTTTTTCACTATCAGACGGCTCGAAGCCCTCTCGACGCCATTTTT

1631 TAAGGTTGCTTTGCAAGACTAGTCGCTTCAAGCATAGCCGCAACAACTGAT
     ATTCCAACGAAACGTTCTGATCAGCGAAGTTCGTATCGGCGTTGTTGACTA

1682 CCGTTATTGTTTGCCGCGAAAAACGATTAAATTTGGACCGCTTGTGTTGG
     GGCAATAACAAACGGGCTTTTTGCTAATTTAAACCTGGCGAACACAACC

FIG. 2E

```
1733  TCTAAATTGGCAAAAACGGCTTGTTGATACCAATCATTTAATACTTTCACT
      AGATTTAACCGTTTTTGCCGAACAACTATGGTTAGTAAATTATGAAAGTGA

1784  ATCGGTTCGTTACGGAAACGTTTCGCCCATTGATGGTCGTTTTGCCAACGA
      TAGCCAAGCAATGCCTTTGCAAAGCGGGTAACTACCAGCAAAACGGTTGCT

1835  GCTTGGCGTTCCTCATCTGTTGCTAAGCCGATGTTCGCTCCTTCAAGAATC
      CGAACCGCAAGGAGTAGACAACGATTCGGCTACAAGCGAGGAAGTTCTTAG

1886  GTATGTTTTAGCTGAGGATTATTGGCATTGAGCGCATAGTCAACGCTAAAC
      CATACAAAATCGACTCCTAATAACCGTAACTCGCGTATCAGTTGCGATTTG

1937  GCCCGCCTAACGAATAGCCGACCAAATAAAAAGGCTGATTGCCGATATAAT
      CGGGCGGATTGCTTATCGGCTGGTTTATTTTTCCGACTAACGGCTATATTA

1988  GCAGAACGGTTTGATGAATCAATTCTCTCGTGTGGGAAAAGCCGTAGCAGG
      CGTCTTGCCAAACTACTTAGTTAAGAGAGCACACCCTTTTCGGCATCGTCC

2039  GGATATGTTCGCTTGCCGCCATGCAGAGGAAGGTCAATGGTAAGCGGTCGA
      CCTATACAAGCGAACGGGTACGTCTCCTTCCAGTTACCATTCGCCAGCT

2090  ATTTGCGGAAAANNNNNCTAGCACCGCTTGCCAAATCTTGTTGCGAACCGA
      TAAACGCCTTTTNNNNNGATCGTGGCGAACGTTTAGAACAACGCTTGGCT
```

FIG. 2F

```
2141  GTAAACCGTGCAGGAAAAAACCACCGGCATACCCGTTTCACGATGCCATGT
      CATTTGGCACGTCCTTTTTTGGTGGCCCGTATGGGCAAAGTGCTACGGTACA

2192  TGCGTGGAGCATTAGGCAATTTCCGCTTGTGAGATTTGTTTAACTAAGGAT
      ACGCACCTCGTAATCCGTTAAAGGCGAACACTCTAAACAAATTGATTCCTA

2243  TTGTAAAGATTGCTACCGTCTTGATCGTTCACTTTAATTTCAACGCATAGT
      AACATTTCTAACGATGGCAGAACTAGCAAGTGAAATTAAAGTTGCGTATCA

2294  CACGCCCTTTACGTCCGTAAGCGGAGTTTCAGTTTCGCTTTCAGATCGGCCCA
      GTGCGGAAATGCAGGCATTCGCCTCAAAGTCAAAGCGAAAGTCTAGCCGGGT

2345  AGTAAACGGACGGATATATTCAATGCCGAATATGGTCGCAATCGGTGCGAA
      TCATTTGCCTGCCTATATAAGTTACGGCTTATACCAGCGTTAGCCACGCTT

2396  TTC
      AAG
```

FIG. 2G

ACTINOBACILLUS PLEUROPNEUMONIAE OUTER MEMBRANE LIPOPROTEIN A AND USES THEREOF

TECHNICAL FIELD

The instant invention relates generally to the prevention of disease in swine. More particularly, the present invention relates to subunit vaccines for *Actinobacillus pleuropneumoniae*.

BACKGROUND

*Actinobacillus* (formerly *Haemophilus*) *pleuropneumoniae* is a highly infectious porcine respiratory tract pathogen that causes porcine pleuropneumonia. Infected animals develop acute fibrinous pneumonia which leads to death or chronic lung lesions and reduced growth rates. Infection is transmitted by contact or aerosol and the morbidity in susceptible groups can approach 100%. Persistence of the pathogen in clinically healthy pigs also poses a constant threat of transmitting disease to previously uninfected herds.

The rapid onset and severity of the disease often causes losses before antibiotic therapy can become effective. Presently available vaccines are generally composed of chemically inactivated bacteria combined with oil adjuvants. However, whole cell bacterins and surface protein extracts often contain immunosuppressive components which make pigs more susceptible to infection. Furthermore, these vaccines may reduce mortality but do not reduce the number of chronic carriers in a herd.

There are at least 12 recognized serotypes of *A. pleuropneumoniae* with the most common in North America being serotypes 1, 5 and 7. Differences among serotypes generally coincide with variations in the electrophoretic mobility of outer membrane proteins and enzymes, thus indicating a clonal origin of isolates from the same serotype. This antigenic variety has made the development of a successful vaccination strategy difficult. Protection after parenteral immunization with a killed bacterin or cell free extract is generally serotype specific and does not prevent chronic or latent infection. Higgins, R., et al., *Can. Vet. J.* (1985) 26:86–89; MacInnes, J. I. and Rosendal, S., *Infect. Immun.* (1987) 55:1626–1634. Thus, it would be useful to develop vaccines which protect against both death and chronicity and do not have immunosuppressive properties. One method by which this may be accomplished is to develop subunit antigen vaccines composed of specific proteins in pure or semi-pure form.

An increasing number of bacterial antigens have now been identified as lipoproteins (Anderson, B. E., et al., *J. Bacteriol.* (1988) 70:4493–4500; Bricker, T. M., et al., *Infect. Immun.* (1988) 56:295–301; Hanson, M. S., and Hansen, E. J., *Mol. Microbiol.* (1991) 5:267–278; Hubbard, C. L., et al., *Infect. Immun.* (1991) 59:1521–1528; Nelson, M. B., et al., *Infect. Immun.* (1988) 56:128–134; Thirkell, D., et al., *Infect. Immun.* (1991) 59:781–784). One such lipoprotein from *Haemophilus somnus* has been positively identified. The nucleotide sequence for this lipoprotein, termed "LppA," has been determined (Theisen, M., et al., *Infect. Immun.* (1992) 60:826–831). These lipoproteins are generally localized in the envelope of the cell and are therefore exposed to the host's immune system. It has been shown that the murine lipoprotein from the outer membrane of *Escherichia coli* acts as a potent activator of murine lymphocytes, inducing both proliferation and immunoglobulin secretion (Bessler, W., et al., *Z. Immun.* (1977) 153:11–22; Melchers, F., et al., *J. Exp. Med.* (1975) 142:473–482). The active lipoprotein portion of the protein has been shown to reside in the N-terminal fatty acid containing region of the protein. Recent studies using synthetic lipopeptides based on this protein show that even short peptides, containing two to five amino acids covalently linked to palmitate, are able to activate murine lymphocytes (Bessler, W. G., et al., *J. Immunol.* (1985) 35:1900–1905).

It has been found that *A. pleuropneumoniae* possesses several outer membrane proteins which are expressed only under iron limiting growth conditions (Deneer, H. G., and Potter, A. A., *Infect. Immun.* (1989) 57:798–804). However, outer membrane lipoproteins from *A. pleuropneumoniae* have not heretofore been identified or characterized with respect to their immunogenic or protective capacity.

DISCLOSURE OF THE INVENTION

The present invention is based on the discovery of a novel subunit antigen from *A. pleuropneumoniae* which shows protective capability in pigs.

Accordingly, in one embodiment, the subject invention is directed to purified, immunogenic *A. pleuropneumoniae* outer membrane lipoprotein A, or an immunogenic fragment thereof.

In another embodiment, the instant invention is directed to an isolated nucleotide sequence comprising a sequence encoding an immunogenic *A. pleuropneumoniae* outer membrane lipoprotein A, or an immunogenic fragment thereof.

In yet another embodiment, the subject invention is directed to a DNA construct comprising the above nucleotide sequence and control sequences that are operably linked to the nucleotide sequence whereby the nucleotide sequence can be transcribed and translated in a host cell, and at least one of the control sequences is heterologous to the nucleotide sequence.

In still further embodiments, the instant invention is directed to host cells transformed with these constructs and methods of recombinantly producing the subject *A. pleuropneumoniae* proteins.

In another embodiment, the subject invention is directed to a vaccine composition comprising a pharmaceutically acceptable vehicle and an *A. pleuropneumoniae* outer membrane lipoprotein A or an immunogenic fragment thereof.

In still another embodiment, the invention is directed to a method of treating or preventing an *A. pleuropneumoniae* infection in a vertebrate subject comprising administering to the subject a therapeutically effective amount of a vaccine composition as described above.

These and other embodiments of the present invention will readily occur to those of ordinary skill in the art in view of the disclosure herein.

BRIEF DESCRIPTION OF THE FIGURES

FIGS. 1A–1E depict the nucleotide sequence of the gene coding for *A. pleuropneumoniae* serotype 1 outer membrane lipoprotein A as well as the nucleotide sequence from the flanking regions from the HB101/pOM37/E16 clone (SEQ ID: 1). The predicted amino acid sequence is also shown.

FIGS. 2A–2G depict the nucleotide sequence of the gene encoding for *A. pleuropneumoniae* serotype 5 outer membrane lipoprotein A as well as the nucleotide sequence for the flanking regions from HB101/pSR213/E25 (SEQ ID: 2). The predicted amino acid sequence is also shown.

DETAILED DESCRIPTION

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, *Molecular Cloning: A Laboratory Manual*, Second Edition (1989); *DNA Cloning*, Vols. I and II (D. N. Glover, ed., 1985); *Oligonucleotide synthesis* (M. J. Gait, ed., 1984); *Nucleic Acid Hybridization* (B. D. Hames & S. J. Higgins, eds., 1984); *Animal Cell Culture* (R. K. Freshney, ed., 1986); *Immobilized Cells and Enzymes* (IRL press, 1986); Perbal, B., *A Practical Guide to Molecular Cloning* (1984); the series, *Methods In Enzymology* (S. Colowick and N. Kaplan, eds., Academic Press, Inc.); and *Handbook of Experimental Immunology*, Vols. I–IV (D. M. Weir and C. C. Blackwell, eds., 1986, Blackwell Scientific Publications).

All patents, patent applications and publications cited herein, whether supra or infra, are hereby incorporated by reference in their entirety.

A. Definitions

In describing the present invention, the following terms will be employed, and are intended to be defined as indicated below.

The terms "outer membrane lipoprotein A" and "OmlA" are equivalent and interchangeable and define a protein from the family of proteins represented by *A. pleuropneumoniae* serotype 1 OmlA (depicted in FIG. 1) and *A. pleuropneumoniae* serotype 5 OmlA (depicted in FIG. 2). The term "OmlA" also captures proteins substantially homologous and functionally equivalent to native OmlAs. Thus, the term encompasses modifications, such as deletions, additions and substitutions (generally conservative in nature), to the native sequences, as long as immunological activity (as defined below) is not destroyed. Such modifications of the primary amino acid sequence may result in antigens which have enhanced activity as compared to the native sequence. These modifications may be deliberate, as through site-directed mutagenesis, or may be accidental, such as through mutations of hosts which produce the lipoprotein. All of these modifications are included, so long as immunogenic activity is retained. Accordingly, *A. pleuropneumoniae* serotype 1 OmlA and *A. pleuropneumoniae* serotype 5 OmlA refer not only to the amino acid sequences depicted in FIGS. 1 and 2, repectively, but to amino acid sequences homologous thereto which retain the defined immunological activity.

Additionally, the term "OmlA" (or fragments thereof) denotes a protein which occurs in neutral form or in the form of basic or acid addition salts, depending on the mode of preparation. Such acid salts may involve free amino groups and basic salts may be formed with free carboxyls. Pharmaceutically acceptable basic and acid addition salts are discussed further below. In addition, the protein may be modified by combination with other biological materials such as lipids (either those normally associated with the lipoprotein or other lipids that do not destroy activity) and saccharides, or by side chain modification, such as acetylation of amino groups, phosphorylation of hydroxyl side chains, or oxidation of sulfhydryl groups, as well as other modifications of the encoded primary sequence. Thus, included within the definition of "OmlA" herein are glycosylated and unglycosylated forms, the amino acid sequences with or without associated lipids, and amino acid sequences substantially homologous to the native sequence which retain the ability to elicit an immune response.

Two DNA or polypeptide sequences are "substantially homologous" when at least about 65% (preferably at least about 80% to 90%, and most preferably at least about 95%) of the nucleotides or amino acids match over a defined length of the molecule. As used herein, substantially homologous also refers to sequences showing identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, vols I & II, supra; *Nucleic Acid Hybridiation*, supra.

The term "functionally equivalent" intends that the amino acid sequence of the subject protein is one that will elicit an immunological response, as defined below, equivalent to or better than, the immunological response elicited by a native *A. pleuropneumoniae* OmlA.

An "antigen" refers to a molecule containing one or more epitopes that will stimulate a host's immune system to make a humoral and/or cellular antigen-specific response. The term is also used interchangeably with "immunogen."

By "subunit antigen" is meant an antigen entity separate and discrete from a whole bacterium (live or killed). Thus, an antigen contained in a cell free extract would constitute a "subunit antigen" as would a substantially purified antigen.

A "hapten" is a molecule containing one or more epitopes that does not stimulate a host's immune system to make a humoral or cellular response unless linked to a carrier.

The term "epitope" refers to the site on an antigen or hapten to which a specific antibody molecule binds. The term is also used interchangeably with "antigenic determinant" or "antigenic determinant site."

An "immunological response" to an antigen or vaccine is the development in the host of a cellular and or antibody-mediated immune response to the composition or vaccine of interest. Usually, such a response includes but is not limited to one or more of the following effects; the production of antibodies, B cells, helper T cells, suppressor T cells, and/or cytotoxic T cells and-/or γδ T cells, directed specifically to an antigen or antigens included in the composition or vaccine of interest.

The terms "immunogenic polypeptide" and "immunogenic amino acid sequence" refer to a polypeptide or amino acid sequence, respectively, which elicit antibodies that neutralize bacterial infectivity, and/or mediate antibody-complement or antibody dependent cell cytotoxicity to provide protection of an immunized host. An "immunogenic polypeptide" as used herein, includes the full length (or near full length) sequence of an *A. pleuropneumoniae* OmlA, or an immunogenic fragment thereof. By "immunogenic fragment" is meant a fragment of an *A. pleuropneumoniae* OmlA which includes one or more epitopes and thus elicits antibodies that neutralize bacterial infectivity, and/or mediate antibody-complement or antibody dependent cell cytotoxicity to provide protection of an immunized host. Such fragments will usually be at least about 5 amino acids in length, and preferably at least about 10 to 15 amino acids in length. There is no critical upper limit to the length of the fragment, which could comprise nearly the full length of the protein sequence, or even a fusion protein comprising fragments of two or more of the *A. pleuropneumoniae* subunit antigens.

The terms "polypeptide" and protein are used interchangeably and refer to any polymer of amino acids (dipeptide or greater) linked through peptide bonds. Thus, the terms "polypeptide" and "protein" include oligopeptides, protein fragments, analogs, muteins, fusion proteins and the like.

"Native" proteins or polypeptides refer to proteins or polypeptides recovered from a source occurring in nature. Thus, the term "native outer membrane lipoprotein A" would include naturally occurring OmlA and fragments of these proteins.

By "purified protein" is meant a protein separate and discrete from a whole organism (live or killed) with which the protein is normally associated in nature. Thus, a protein contained in a cell free extract would constitute a "purified protein," as would a protein synthetically or recombinantly produced.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-strandedDNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence" or a "nucleotide sequence encoding" a particular protein, is a DNA sequence which is transcribed and translated into a polypeptide in vivo or in vitro when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Dalgarno sequences in addition to the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A control sequence "directs the transcription" of a coding sequence in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

A composition containing A is "substantially free of" B when at least about 85% by weight of the total of A+B in the composition is A. Preferably, A comprises at least about 90% by weight of the total of A+B in the composition, more preferably at least about 95%, or even 99% by weight.

The term "treatment" as used herein refers to either (i) the prevention of infection or reinfection (prophylaxis), or (ii) the reduction or elimination of symptoms of the disease of interest (therapy).

B. General Methods

Central to the present invention is the discovery of a family of A. pleuropneumoniae outer membrane lipoproteins, termed OmlAs herein, which are able to elicit an immune response in an animal to which they are administered. All 12 of the A. pleuropneumoniae serotypes appear to contain a gene encoding an OmlA. This protein, analogs thereof and/or immunogenic fragments derived from the protein, are provided in subunit vaccine compositions and thus problems inherent in prior vaccine compositions, such as localized and systemic side reactions, as well as the inability to protect against chronic disease, are avoided. The vaccine compositions can be used to treat or prevent A. pleuropneumoniae-induced respiratory diseases in swine such as porcine pleuropneumonia. The antigens or antibodies thereto can also be used as diagnostic reagents to detect the presence of an A. pleuropneumoniae infection in a subject. Similarly, the genes from the various serotypes encoding the OmlA proteins can be cloned and used to design probes for the detection of A. pleuropneumoniae in tissue samples as well as for the detection of homologous genes in other bacterial strains. The subunit antigens can be conveniently produced by recombinant techniques, as described herein. The proteins of interest are produced in high amounts in transformants, do not require extensive purification or processing, and do not cause lesions at the injection site or other ill effects.

The genes encoding the A. pleuropneumoniae serotype 1 OmlA and serotype 5 OmlA have been isolated and the sequences are depicted in FIG. 1 (SEQ ID NO: 1) and FIG. 2 (SEQ ID NO: 2), respectively. The nucleotide sequence for the serotype 1 omlA gene, including the structural gene and flanking regions, consists of approximately 1340 base pairs. The open reading frame codes for a protein having approximately 365 amino acids. The nucleotide sequence for the serotype 5 omlA gene, including the structural gene and flanking regions, consists of approximately 2398 base pairs. The structural gene codes for a protein of approximately 367 amino acidS. The serotype 1 and serotype 5 OmlA proteins are approximately 65% homologous.

The omlA gene from A. pleuropneumoniae serotype 1 hybridizes with genomic DNA from all other known A. pleuropneumoniae serotypes. The invention, therefore, encompasses genes encoding OmlA from all of the A. pleuropneumoniae serotypes.

The full-length serotype 1 and serotype 5 lipoproteins both have an apparent molecular mass of approximately 50 kDa, as determined by discontinuous sodium dodecylsulfate-polyacrylamide gel electrophoresis (SDS-PAGE) according to the method of Laemmli (Laemmli, M. K., Nature (1970) 227:680–685). The predicted molecular weights, based on the amino acid sequences, are 39,780 and 40,213, respectively. The recombinantly produced proteins are able to protect pigs from subsequent challenge with A. pleuropneumoniae. Other OmlA proteins, from other A. pleuropneumoniae serotypes, can also be identified, purified and sequenced, using any of the various methods known-to those skilled in the art. For example, the amino acid sequences of the subject proteins can be determined from the purified proteins by repetitive cycles of Edman degradation, followed by amino acid analysis by HPLC. Other methods of amino acid sequencing are also known in the art. Fragments of the purified proteins can be tested for biological activity and active fragments, as described above, used in compositions in lieu of the entire protein.

In order to identify genes encoding the subject proteins, recombinant techniques can be employed. For example a DNA library can be prepared which consists of genomic DNA from an A. pleuropneumoniae serotype. The resulting clones can be used to transform an appropriate host, such as E. coli. Individual colonies can then be screened in an immunoblot assay, using polyclonal serum or monoclonal antibodies, to the desired antigen.

More specifically, after preparation of a DNA library, DNA fragments of a desired length are isolated by, e.g., sucrose density gradient centrifugation. These fragments are then ligated into any suitable expression vector or replicon and thereafter the corresponding host cell is transformed with the constructed vector or replicon. Transformed cells are plated in suitable medium. A replica plate must also be prepared because, subsequent procedures kill these colonies. The colonies are then lysed in one of a number of ways, e.g., by exposure to chloroform vapor. This releases the antigen from the positive colonies. The lysed colonies are incubated with the appropriate unlabelled antibody and developed using an appropriate anti-immunoglobulin conjugate and substrate. Positively reacting colonies thus detected can be recovered from the replica plate and subcultured. Physical mapping, construction of deletion derivatives and nucleotide sequencing can be used to characterize the encoding gene.

An alternative method to identify genes encoding the proteins of the present invention, once the genomic DNA library is constructed as described above, is to prepare oligonucleotides to probe the library and to use these probes to isolate the gene encoding the desired protein. The basic strategies for preparing oligonucleotide probes, as well as screening libraries using nucleic acid hybridization, are well known to those of ordinary skill in the art.. See, e.g., DNA Cloning: Vol. I, supra; Nucleic Acid Hybridization, supra; Oligonucleotide Synthesis, supra; Sambrook et al., supra. The particular nucleotide sequences selected are chosen so as to correspond to the codons encoding a known amino acid sequence from the desired protein. Since the genetic code is degenerate, it will often be necessary to synthesize several oligonucleotides to cover all, or a reasonable number of, the possible nucleotide sequences which encode a particular region of the protein. Thus, it is generally preferred in selecting a region upon which to base the probes, that the region not contain amino acids whose codons are highly degenerate. In certain circumstances, one of skill in the art may find it desirable to prepare probes that are fairly long, and/or encompass regions of the amino acid sequence which would have a high degree of redundancy in corresponding nucleic acid sequences, particularly if this lengthy and/or redundant region is highly characteristic of the protein of interest. It may also be desirable to use two probes (or sets of probes), each to different regions of the gene, in a single hybridization experiment. Automated oligonucleotide synthesis has made the preparation of large families of probes relatively straight-forward. While the exact length of the probe employed is not critical, generally it is recognized in the art that probes from about 14 to about 20 base pairs are usually effective. Longer probes of about 25 to about 60 base pairs are also used.

The selected oligonucleotide probes are labeled with a marker, such as a radionucleotide or biotin using standard procedures. The labeled set of probes is then used in the screening step, which consists of allowing the single-stranded probe to. hybridize to isolated ssDNA from the library, according to standard techniques. Either stringent or permissive hybridization conditions could be appropriate, depending upon several factors, such as the length of the probe and whether the probe is derived from the same species as the library, or an evolutionarily close or distant species. The selection of the appropriate conditions is within the skill of the art. See, generally, *Nucleic Acid hybridization*, supra. The basic requirement is that hybridization conditions be of sufficient stringency so that selective hybridization occurs; i.e., hybridization is due to a sufficient degree of nucleic acid homology (e.g., at least about 75%), as opposed to nonspecific binding. Once a clone from the screened library has been identified by positive hybridization, it can be confirmed by restriction enzyme analysis and DNA sequencing that the particular library insert contains a gene for the desired protein.

Alternatively, DNA sequences encoding the proteins of interest can be prepared synthetically rather than cloned. The DNA sequence can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al., (1984) *Science* 223:1299; Jay et al., (1984) *J. Biol. Chem.* 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, *DNA Cloning*: Vols. I & II, supra; Sambrook et al., supra; B. Perbal, supra.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. Leader sequences can be removed by the host in post-translational processing. See, e.g., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular antigen of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal. It may also be desirable to produce mutants or analogs of the antigens of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known-to those skilled in the art. See, e.g., Sambrook et al., supra; *DNA Cloning*, Vols. I and II, supra; *Nucleic Acid Hybridization*, supra.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491.

Depending on the expression system and host selected, the proteins of the present invention are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art.

OmlA antigens can also be isolated directly from any of the *A. pleuropneumoniae* serotypes. This is generally accomplished by first preparing a crude extract which lacks cellular components and several extraneous proteins. The desired antigens can then be further purified, i.e., by column chromatography, HPLC, immunoadsorbent techniques or other conventional methods well known in the art.

The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides may be preferable if a small fragment of the antigen in question is capable of raising an immunological response in the subject of interest.

The proteins of the present invention or their fragments can be used to produce antibodies, both polyclonal and monoclonal. If polyclonal antibodies are desired, a selected mammal, (e.g., mouse, rabbit, goat, horse, pig etc.) is immunized with an antigen of the present invention, or its fragment, or a mutated antigen. Serum from the immunized animal is collected and treated according to known procedures. If serum containing polyclonal antibodies is used, the polyclonal antibodies can be purified by immunoaffinity chromatography, using known procedures.

Monoclonal antibodies to the proteins of the present invention, and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the antigen of interest, or fragment thereof, can be screened for various properties; i.e., for isotype, epitope, affinity, etc. Monoclonal antibodies are useful in purification, using immunoaffinity techniques, of the individual antigens which they are directed against.

Animals can be immunized with the compositions of the present invention by administration of the protein of interest, or a fragment thereof, or an analog thereof. If the fragment or analog of the protein is used, it will include the amino acid sequence of an epitope which interacts with the immune system to immunize the animal to that and structurally similar epitopes.

If synthetic or recombinant proteins are employed, the subunit antigen can be a single polypeptide encoding one or several epitopes from one or more OmlAs or two or more discrete polypeptides encoding different epitopes. The subunit antigen, even though carrying epitopes derived from a lipoprotein, does not require the presence of the lipid moiety. However, if the lipid is present, it need not be a lipid commonly associated with the lipoprotein, so long as the appropriate immunologic response is elicited.

Prior to immunization, it may be desirable to increase the immunogenicity of the particular protein, or an analog of the protein, or particularly fragments of the protein. This can be accomplished in any one of several ways known to those of skill in the art. For example, the antigenic peptide may be administered linked to a carrier. Suitable carriers are typically large, slowly metabolized macromolecules such as: proteins; polysaccharides, such as sepharose, agarose, cellulose, cellulose beads and the like; polymeric amino acids such as polyglutamic acid, polylysine, and the like; amino acid co-polymers; and inactive virus particles. Especially useful protein substrates are serum albumins, keyhole limpet hemocyanin, immunoglobulin molecules, thyroglobulin, ovalbumin, and other proteins well known to those skilled in the art.

The protein substrates may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Other suitable carriers for the proteins of the present invention include VP6 polypeptides of rotaviruses, or functional fragments thereof, as disclosed in allowed U.S. Pat. No. 5,071,651 and incorporated herein by reference. Also useful is a fusion product of a viral protein and the subject immunogens made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the proteins of the present invention may be coupled to erythrocytes, preferably the subject's own erythrocytes. Methods of coupling peptides to proteins or cells are known to those of skill in the art.

The novel proteins of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel proteins can be constructed as follows. The DNA encoding the particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting TK$^-$ recombinant can be selected by culturing the cells in the presence of 5-bromodeoxyuridine and picking viral plaques resistant thereto.

It is also possible to immunize a subject with a protein of the present invention, or a protective fragment thereof, or an analog thereof, which is administered alone, or mixed with a pharmaceutically acceptable vehicle or excipient. Typically, vaccines are prepared as injectables, either as liquid solutions or suspensions; solid forms suitable for solution in, or suspension in, liquid vehicles prior to injection may also be prepared. The preparation may also be emulsified or the active ingredient encapsulated in liposome vehicles. The active immunogenic ingredient is often mixed with vehicles containing excipients which are pharmaceutically acceptable and compatible with the active ingredient. Suitable vehicles are, for example, water, saline, dextrose, glycerol, ethanol, or the like, and combinations thereof. In addition, if desired, the vehicle may contain minor amounts of auxiliary substances such as wetting or emulsifying agents, pH buffering agents, or adjuvants which enhance the effectiveness of the vaccine. Adjuvants may include for example, muramyl dipeptides, avridine, aluminum hydroxide, oils, saponins and other substances known in the art. Actual methods of preparing such dosage forms are known, or will be apparent, to those skilled in the art. See, e.g., *Remington's Pharmaceutical Sciences*, Mack Publishing Company, Easton, Penn., 15th edition, 1975. The composition or formulation to be administered will, in any event, contain a quantity of the protein adequate to achieve the desired immunized state in the individual being treated.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither causeirritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and Hytrel ® copolymers, swellable polymers such as hydrogels, or resorbable polymers such as collagen and certain polyacids or polyesters such as those used to make resorbable sutures. The proteins can also be delivered using implanted mini-pumps, well known in the art.

Furthermore, the proteins (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

To immunize a subject, the polypeptide of interest, or an immunologically active fragment thereof, is administered parenterally, usually by intramuscular injection in an appropriate vehicle. Other modes of administration, however, such as subcutaneous, intravenous injection and intranasal delivery, are also acceptable. Injectable vaccine formulations will contain an effective amount of the active ingredient in a vehicle, the exact amount being readily determined by one skilled in the art. The active ingredient may typically range from about 1% to about 95% (w/w) of the composition, or even higher or lower if appropriate. The quantity to be administered depends on the animal to be treated, the capacity of the animal's immune system to synthesize antibodies, and the degree of protection desired. With the present vaccine formulations, as little as 0.1 to 100 $\mu$g or more, preferably 0.5 to 50 $\mu$g, more preferably 1.0 to 25 $\mu$g, of active ingredient per ml of injected solution, should be adequate to raise an immunological response when a dose of 1 to 2 ml per animal is administered. Other effective dosages can be readily established by one of ordinary skill in the art through routine trials establishing dose response curves. The subject is immunized by administration of the particular antigen or fragment thereof, or analog thereof, in at least one dose, and preferably two doses. Moreover, the animal may be administered as many doses as is required to maintain a state of immunity to pneumonia.

An alternative route of administration involves gene therapy or nucleic acid immunization. Thus, nucleotide sequences (and accompanying regulatory elements) encoding the subject proteins can be administered directly to a subject for in vivo translation thereof. Alternatively, gene transfer can be accomplished by transfecting the subjects cells or tissues ex vivo and reintroducing the transformed material into the host. DNA can be directly introduced into the host organism, i.e., by injection (see International Publication No. WO/90/11092; and Wolff et al., *Science* (1990) 247:1465–1468). Liposome-mediated gene transfer can also be accomplished using known methods. See, e.g., Hazinski et al., *Am. J. Respir. Cell Mol. Biol.* (1991) 4:206–209; Brigham et al., *Am. J. Med. Sci.* (1989) 298:278–281; Canonico et al., *Clin. Res.* (1991) 39:219A; and Nabel et al., *Science* (1990) 249:1285–1288. Targeting agents, such as antibodies directed against surface antigens expressed on specific cell types, can be covalently conjugated to the liposomal surface so that the nucleic acid can be delivered to specific tissues and cells susceptible to *A. pleuropneumoniae*.

Below are examples of specific embodiments for carrying out the present invention. The examples are offered for illustrative purposes only, and are not intended to limit the scope ok the present invention in any way.

Deposits of strains Useful in Practicing the Invention

A deposit of biologically pure cultures of the following strains was made with the American Type Culture Collection, 12301 Parklawn Drive, Rockville, Md. The accession number indicated was assigned after successful viability testing, and the requisite fees were paid.

Access to said cultures will be available during pendency of the patent application to one determined by the Commissioner to be entitled thereto under 37 CFR 1.14 and 35 USC §122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

These deposits are provided merely as a convenience to those of skill in the art, and are not an admission that a deposit is required under 35 USC §S112. The nucleic acid sequences of these plasmids, as well as the amino acid sequences of the polypeptides encoded thereby, are incorporated herein by reference and are controlling in the event of any conflict with the description herein. A license may be required to make, use, or sell the deposited materials, and no such license is hereby granted.

| Strain | Deposit Date | ATCC No. |
|---|---|---|
| HB101/pOM37/E1 (in E. coli) | 4/7/92 | 68954 |
| HB101/pSR213/E25 (in E. coli) | 10/8/92 | 69083 |

C. Experimental

Materials and Methods

Enzymes were purchased from commercial sources, and used according to the manufacturers' directions. Radionucleotides and nitrocellulose filters were also purchased from commercial sources.

In the cloning of DNA fragments, except where noted, all DNA manipulations were done according to standard procedures. See Sambrook et al., supra. Restriction enzymes, $T_4$ DNA ligase, E. coli, DNA polymerase I, Klenow fragment, and other biological reagents were purchased from commercial suppliers and used according to the manufacturers' directions. Double stranded DNA fragments were separated on agarose gels.

Bacterial Strains, Plasmids and Media

A. pleuropneumoniae serotype 1 strain AP37 and A. pleuropneumoniae serotype 5 strain AP213 were isolated from the lungs of diseased pigs given to the Western College of Veterinary Medicine, University of Saskatchewan, Saskatoon, Saskatchewan, Canada. A. pleuropneumoniae serotype 7 strain AP205 was a Nebraska clinical isolate obtained from M. L. Chepok, Modern Veterinary Products, Omaha, Nebr. Other A. pleuropneumoniae strains were field isolates from herds in Saskatchewan. The E. coli strain HB101 (hsdM, hsdR, recA) was used in all transformations using plasmid DNA. E. coli strains NM538 (supF, hsdR) and NM539 (supF, hsdR, P2cox) served as hosts for the bacteriophage λ library. The plasmids pGH432 and pGH433 are expression vectors containing a tac promoter, a translational start site with restriction enzyme sites allowing ligation in all three reading frames followed by stop codons in all reading frames.

A. pleuropneumoniae strains were grown on PPLO medium (Difco Laboratories, Detroit, Mich.) supplemented with 10 mg/ml β-nicotinamide adenine dinucleotide (Sigma Chemical Co., St. Louis, Mo.). Plate cultures were incubated in a $CO_2$-enriched (5%) atmosphere at 37° C. Liquid cultures were grown with continuous shaking at 37° C. without $CO_2$ enrichment.

Iron restriction was obtained by adding 2,2'-dipyridyl to a final concentration of 100 μmol. E. coli transformants were grown in Luria medium (Sambrook et al., supra) supplemented with ampicillin (100 mg/l). Transcription from the tac-promoter was induced by the addition of isopropylthioglactopyranoside (IPTG) to a final concentration of 1 mmol.

Preparation and Analysis of Culture Supernatants, Outer Membranes and Protein Aggregates.

Culture supernatants, outer membranes, and aggregated protein were prepared as previously described (Gerlach et al., Infect. Immun. (1992) 60:892–898; Deneer, H. G., and Potter, A. A., Infect. Immun. (1989) 57:798–804). Culture supernatants were mixed with two volumes of absolute ethanol and kept at −20° C. for 1 h. Precipitates were recovered by centrifugation and resuspended in water. Outer membranes were prepared by sarkosyl solubilization as previously described (Deneer and Potter, supra). For the preparation of protein aggregates, broth cultures (50 ml) in mid log phase ($OD_{660}$ of 0.6) were induced by the addition of 1 mmol isopropylthiogalactoside (IPTG; final concentration). After 2 hours of vigorous shaking at 37° C., cells were harvested by centrifugation, resuspended in 2 ml of 25% sucrose, 50 mmol Tris/HCl buffer pH 8, and frozen at −70° C. Lysis was achieved by the addition of 5 μg of lysozyme in 250 mmol Tris/HCl buffer pH 8 (5 min on ice), addition of 10 ml detergent mix (5 parts 20 mmol Tris/HCl buffer pH 8 (5 min on ice), addition of 10 ml detergent mix (5 parts 20 mmol Tris/HCl buffer pH 7.4, 300 mmol NaCl, 2% deoxycholic acid, 2% NP-40, and 4 parts of 100 mmol Tris/HCl buffer pH 8, 50 mmol ethylenediamine tetraacetic acid, 2% Triton X-100), and by sonication. Protein aggregates were harvested by centrifugation for 30 min at 15,000 g. Aggregate protein was resuspended in $H_2O$ to a concentration of 5–10 mg/ml and solubilized by the addition of an equal volume of 7 molar guanidine hydrochloride. The concentration of protein in the aggregate preparations was determined by separating serial dilutions of the protein using SDS-PAGE. The intensity of the Coomassie blue stained bands was compared with those of a bovine serum albumin standard (Pierce Chemical Co., Rockford, Ill.).

Western Blotting

Whole cell lysates of A. pleuropneumoniae grown in broth under iron-restricted conditions were separated by SDS-PAGE and electroblotted onto nitrocellulose membranes essentially as described by Towbin et al. (Towbin et al., Proc. Natl. Acad. Sci. U.S.A. (1979) 76:4350–4354). Nonspecific binding was blocked by incubation in 0.5% gelatine in washing buffer (150 mmol saline, 30 mmol Tris-HCl, 0.05% Triton-X100). Antibody and alkaline phosphatase conjugate (Kirkegaard & Perry Laboratories, Inc., Gaithersburg, Md.) were added in washing buffer, and each incubated for 1 h at room temperature. Blots were developed with a substrate containing 5-bromo-4-chloro-3-indolyl phosphate (BCIP) and nitro blue tetrazolium (NBT) (ImmunoSelect, BRL, Gaithersburg, Md.) in 100 mmol Tris/HCl buffer pH 9.5, 50 mmol NaCl, 5 mmol $MgCl_2$.

Preparation of Antisera

Serum against an *A. pleuropneumoniae* culture supernatant was obtained as follows. *A. pleuropneumoniae* serotype 1 culture supernatant was precipitated with trichloroacetic (TCA; vol/vol), emulsified with incomplete Freund's adjuvant, and used to immunize rabbits twice at three-week intervals. Porcine convalescent sera were obtained from pigs experimentally infected intranasally by aerosol with *A. pleuropneumoniae* serotype 1 strain AP37.

Preparation of DNA and Southern Blotting

Genomic DNA was prepared by SDS-facilitated freeze-thaw induced lysis as described previously (Stauffer, G. V., et al., *Gene*, (1981) 4:63-72). Plasmid DNA was prepared from 100 µg/ml chloramphenicol-amplified cultures by alkaline lysis and cesium chloride-ethidium bromide gradient centrifugation previously described (Sambrook et al., supra).

Restriction endonuclease digests were done in T4 DNA polymerase buffer (Sambrook et al., supra) supplemented with 1 mmol dithiothreitol and 3 mmol spermidine. Digested DNA was separated on 0.7% agarose gels and transferred onto nitro cellulose by capillary blotting. [$^{32}$P]-labelled probes were prepared by random priming (Feinberg, A. P., and Vogelstein, B. (1983) *Anal. Biochem.* 132:6-13), and unincorporated nucleotides were removed by passage through a Sephadex G-50 column. Filters were prehybridized in 5× Denhardt's solution-6× SSC (1× SSC is 0.15 mol NaCl, 0.015 mol sodium citrate (pH 8))-0.5% SDS at 65° C. Filters were hybridized in the same solution at 55° C. and washed at 55° C. in 3× SSC-0.5% (low stringency), or at 65° C. in 0.1× SSC-0.5% SDS (high stringency).

Preparation and Screening of the *A. pleuropneumoniae* Serotype 1 Expression Library Genomic DNA from *A. pleuropneumoniae* AP37 was partially digested with the restriction endonuclease Sau3AI. Fragments of 3000 Bp to 8000 Bp were isolated by sucrose density gradient centrifugation (Sambrook et al., supra) and ligated into the BamHI and BglII sites of the expression vectors pGH432 and pGH433, thus allowing for fusions in all three reading frames. *E. coli* HB101 was transformed and plated at a density of approximately 400 colonies per plate. Colonies were replica-plated onto nitrocellulose disks, induced for 2 h with 1 mmol IPTG, and lysed in chloroform vapor. Non-specific binding was blocked with 0.5% gelatin in the washing buffer and, after removal of the cellular debris, the membranes were incubated with rabbit serum raised against the *A. pleuropneumoniae* AP37 culture supernatant and developed using goat anti-rabbit conjugate and substrate as described above.

Transposon Mutagenesis

The transposon TnphoA, carried by a lamba phage, as well as the alkaline phosphatase-negative *E. coli* strain CC118, were provided by J. Beckwith, Harvard Medical School, Boston, Mass. The mutagenesis was performed as previously described (Manoil, C., and Beckwith, J. (1985) *Proc. Natl. Acad. Sci. U.S.A.* 82:8129-8133) and the nucleotide sequence at the insertion site was determined using an oligonucleotide primer complementary to the first 20 bases of the phoA-gene in TnphoA (Chang et al. (1986) Gene 44:121-125; Manoil and Beckwith, supra).

Nucleotide Sequence Analysis

DNA sequencing was performed using M13 vectors and the dideoxy chain termination method essentially as described (Sanger, F., et al. (1977) *Proc. Natl. Acad. Sci. U.S.A.* 74:5463-5467). Nested deletions were prepared by exonuclease III treatment (Henikoff, S. (1987) *Methods in Enzymology* 55:156-165). Specific primers were synthesized using the Pharmacia Gene Assembler (Pharmacia Canada Ltd., Baie D'Urfe, Quebec, Canada). Both strands were sequenced in their entirety. The open reading frame (ORF) of the omlA gene was confirmed by TnphoA insertion mutagenesis as described above. The sequence was analyzed using the IBIPustell program and the GenBank database.

Primer Extension Mapping

A was prepared from *A. pleuropneumoniae* AP37 essentially as described by Emory and Belasco (Emory, S. A., and Belasco, J. G. (1990) *J. Bacteriol.* 172:4472-4481). Briefly, 25 ml of bacterial culture ($OD_{660}=0.4$) was cooled on crushed ice and centrifuged. The bacterial pellet was resuspended in 250 µl of 10% sucrose, 10 mM sodium acetate (pH 4.5), and frozen at −70° C. The pellet was thawed by mixing with an equal volume of hot (70° C.) 2% SDS, 10 mM sodium acetate (pH 4.5). Then, 375 µl of hot (70° C.) $H_2O$-equilibrated phenol was added, the tubes were vortexed, frozen at −70° C., and spun for 10 min in an Eppendorf centrifuge. The clear supernatant was removed, 2.5 volumes of ethanol was added, and the RNA was stored at −70° C. until needed. The primer extension was done as described previously using a primer complementary to a sequence within the ORF. 7-Deaza-dGTP and AMV-reverse transcriptase were employed in order to prevent compressions.

Intrinsic Radiolabelling with [$^3$H]-Palmitic Acid, Immunoprecipitation and Globomycin Treatment Labelling was done essentially as described previously (Ichihara, S. et al. (1981) *J. Biol. Chem.* 256:3125-3129). Briefly, [9,10-$^3$H] palmitic acid with a specific radioactivity of 55 Ci/mmol in toluene (Amersham Corp., Arlington Heights, Ill.) was lyophilized and dissolved in isopropanol to a concentration of 5 mCi/ml. *A. pleuropneumoniae* AP37 (in PPLO-broth) and *E. coli* transformants (in Luria broth containing 1 µmol IPTG were grown with methanol, and an immunoprecipitation analysis was performed essentially as previously described (Huang, et al. (1989) *J. Bacteriol.* 171:3767-3774). The OmlA-specific serum was obtained from immunized pigs, and protein G-Sepharose was used to recover the OmlA-porcine antibody complexes. The immunoprecipitated proteins were resuspended in SDS-sample buffer, heated to 80° C. for 5 min and separated by SDS-PAGE. The gels were fixed, treated with Amplify (Amersham Corp., Arlington Heights, Ill.), dried and exposed to X-ray film. Globomycin was dissolved in 50% dimethylsulfoxide at a concentration of 10 mg/ml. This solution was added to an *A. pleuropneumoniae* AP37 culture grown to an $OD_{660}$ of 0.6 to a final concentration of 100 µg/ml. and growth was continued for 1 hour. Cells were pelleted, resuspended in sample buffer and analyzed by SDS-PAGE and electroblotting onto nitrocellulose, as described above, using the OmlA-specific serum.

EXAMPLES

Example 1

Cloning and Expression of the *A. pleuropneumoniae* Serotype 1 omlA Gene

An expression library of *A. pleuropneumoniae* strain AP37 serotype 1 in the vector pGH432 lacI was screened with rabbit polyclonal antiserum generated against a concentrated culture supernatant of *A. pleuropneumoniae* by a colony immunoblot assay as described above. Colonies reacting with serum raised against the culture supernatant were subcultured, induced with IPTG, and examined in a Western blot using porcine convalescent serum. From among those clones which reacted in the colony immunoblot assay, one clone which also reacted with convalescent serum was selected for further study. The *E. coli* transformant produced a protein which co-migrated with an immunoreactive protein from *A. pleuropneumoniae* AP37, and had an electrophoretic mobility of 50 k Da. Upon IPTG induction, this transformant produced the immunoreactive protein in aggregated form. The plasmid encoding this antigen was designated as pOM37/E1 (ATCC Accession No. 68954), and the protein was designated as OmlA.

Physical mapping showed that the plasmid contained a 5,000 Bp insert. Several deletion derivatives were constructed, and it was observed that transformants containing the deletion derivative pOM37/E17 produced a truncated protein, thus indicating that the encoding gene overlaps the KpnI restriction enzyme site.

The nucleotide sequence of the gene encoding OmlA from pOM37/E1 is shown in FIG. 1 (SEQ ID NO: 1). The sequence was determined by dideoxy sequencing of overlapping deletions generated by exonuclease III digestion. The nucleotide sequence has one long open reading frame (ORF) starting at nucleotide position 158 and ending at position 1252. The amino acid sequence of this open reading frame is also shown in FIG. 1 (SEQ ID NO: 1). The predicted polypeptide has a molecular weight of 39,780, with a consensus sequence for lipid modification at amino acid residue 20. In order to confirm this, cells were labelled with [$^3$H]-palmitate and immunoprecipitated with rabbit antisera generated against the recombinant protein as described above. Following polyacrylamide gel electrophoresis and autoradiography, one band with an apparent molecular weight of 50,000 was observed, indicating that lipid modification of the polypeptide had occurred. Further, when globomycin was added, no [$^3$H]-palmitate-labelled material was visible on the autoradiogram. Globomycin is a specific inhibitor of signal peptidase II. Thus, the omlA gene product is a lipoprotein. This may explain why it migrates on polyacrylamide gels with an apparent molecular weight of 50,000 when the predicted value is less than 40,000.

Immunoreactive product was expressed in transformants even in the absence of IPTG induction. This suggests that a promoter recognizable by *E. coli* was located on the *A. pleuropneumoniae*-derived DNA upstream of the ORF. The simultaneous inducibility by IPTG, as well as the truncated polypeptide produced by *E. coli* pOM37/E17 transformants, indicated the location of the carboxy-terminal of the omlA gene as well as its direction of transcription.

Example 2

Analysis of Plasmid pOM37/E16

Colonies reacting with serum raised against the culture supernatant were subcultured, induced with IPTG, and examined in a Western blot as described in Example 1. The smallest plasmid expressing the full-length OmlA protein was designated pOM37/E16. Nucleotide sequence analysis of pOM37/E16 revealed one ORF of 1083 Bp in length coding for a protein with a predicted molecular mass of 39,780 Da. It was preceded by a Shine-Dalgarno consensus sequence AAGGAA 8 Bp upstream of the methionine codon. The protein encoded by the nucleotide sequence of pOM37/E16 is identical to that shown in FIG. 1 (SEQ ID NO: 1).

The first 19 amino acids of the polypeptide have the characteristics of a lipoprotein signal peptide with a predicted cleavage site in front of the cysteine residue at position 20. The ORF was confirmed by two independent TnphoA-insertions 50 bp and 530 bp downstream from the methionine codon which, upon transformation of the phoA-negative *E. coli* strain CC118, gave rise to alkaline phosphatase-positive transformants. A GenBank data base homology search using the predicted amino acid sequence of OmlA did not reveal likely similarities (>35%) to known ORFs or polypeptides.

The primer extension located the beginning of the mRNA at a T-residue 76 Bp upstream of the methionine start codon. The $-10$ and $-30$ regions are both AT-rich, and the promoter-structure matches the *E. coli* consensus characteristics.

One of the TnphoA-insertions was found to be located within the signal peptide. The expression of a functional PhoA protein in this fusion is probably due to its location behind the hydrophobic core of the signal peptide. The transcriptional start site as determined by primer extension analysis is preceded by a $-10$ and $-30$ region similar to those common in *E. coli* promoters, Rosenberg, M., and Court, D., (1979) *Annu. Rev. Genet.* 13:319-353, and this finding is in accordance with the expression found in non-induced *E. coli* transformants. Downstream of the ORF, a palindromic sequence of 26 bp in length is present which might act as a terminator sequence. Adhya, S., and Gottesman, M., (1978) *Annu. Rev. Biochem.* 47:967-996.

The predicted signal peptide cleavage site resulting in an amino-terminal cysteine residue of the mature protein was confirmed by labelling of the *E. coli* transformants with [$^{14}$C]-palmitate and subsequent immunoprecipitation using porcine anti-OmlA serum. In addition, it was shown that growth of *A. pleuropneumoniae* AP37 in the presence of globomycin inhibited the palmitate-labelling of OmlA as well as the processing of the OmlA precursor protein.

The expression of the OmlA protein was independent from the level of iron in the growth medium. The protein was present in whole membranes, outer membranes as prepared by sucrose gradient centrifugation, and membrane blebs; it was absent in sarcosyl-treated outer membranes and in high-speed supernatants.

Example 3

Cloning, Expression and Sequencing of the *A. pleuropneumoniae* Serotype 5 omlA Gene Genomic DNA from *A. pleuropneumoniae* serotype 5 strain AP213 was digested to completion with StyI and ligated into the NcoI site of the pGH432 lacI-derivative, pAA505. HB101 recombinants were screened with convalescent serum obtained from a pig which had been infected with *A. pleuropneumoniae* serotype 5. One positive clone, HB101/pSR213/E1, was selected for further analysis. HB101/pSR213/E1 was shown to contain three StyI fragments. In order to isolate the DNA coding for the immunoreactive protein, StyI fragments from this plasmid were treated with DNA polymerase I Klenow fragment to fill in the 5' extensions. These fragments were ligated into the SmaI site of the vector, pGH432/lacI. A seroreactive clone, designated HB101/pSR213/E4, was isolated and shown to produce a seroreactive protein with an apparent molecular weight of 50 kDa. However, the protein was not expressed at high levels. To increase the level of expression, plasmid pSR213/Er was digested with BglII (which cuts the vector sequence upstream of the gene) and then partially digested with AseI (which cuts at the beginning of the coding region of the gene). The 5' extensions were filled in with DNA polymerase I Klenow fragment, and the plasmid recircularized by ligation. The resulting clone, HB101/pSR213/E25 (ATCC Accession No. 69083), overexpressed the seroreactive protein.

Both strands of the *A. pleuropneumoniae* serotype 5 omlA gene were sequenced using M13 vectors as described above. The nucleotide sequence and predicted amino acid sequence are shown in FIG. 2 (SEQ ID NO: 2). The open reading frame shown in the figure codes for a protein similar to the omlA product of *A. pleuropneumoniae* serotype 1, showing approximately 65% identity at the amino acid level. Thus, the open reading frame present in pSR213/E25 codes for the serotype 5 equivalent of OmlA.

Example 4

Distribution of the QmlA gene in the *A. pleuropneumoniae* type strains.

Genomic DNA from all 12 *A. pleuropneumoniae* type strains was analyzed in a Southern blot using the *A. pleuropneumoniae* AP37-derived omlA-gene as probe. The StyI-restricted DNA from all *A. pleuropneumoniae* type strains reacted with the probe under low stringency conditions, and the DNA from serotypes 1, 2, 8, 9, 11, and 12 remained hybridized to the probe under high stringency washing conditions.

Whole cell lysates from all *A. pleuropneumoniae* type strains, grown under iron-restricted conditions, were analyzed in a Western blot using the serum from pigs immunized with the recombinant OmlA protein. The same strains that hybridized to the DNA probe under high stringency washing conditions bound the anti-OmlA sera, and the whole cell lysates from the *A. pleuropneumoniae* type strains for serotypes 1, 9, and 11 reacted more strongly than those of serotypes 2, 8, and 12.

Example 5

The Protective Capacity of Serotype 1 OmlA Recombinant Protein

The OmlA protein was prepared from *E. coli* HB101/pOM37/E1 by IPTG-induction of a log phase culture followed by cell harvest and disruption, and separation of the inclusion bodies by centrifugation. The inclusion bodies were solubilized with guanidine hydrochloride and mixed with Emulsigen Plus (MVP Laboratories, Ralston, Neb.) and saline so that the final protein concentration was 0.5 µg/ml, 2.5 µg/ml or 12.5 µg/ml. Groups of 7 pigs were vaccinated with 2 ml of the vaccines or a placebo containing Emulsigen Plus but no protein. Each group was revaccinated 21 days later and finally challenged 7 days after the boost with an aerosol of *A. pleuropneumoniae* (serotype 1). Clinical signs of disease were followed for 3 days, and 7 days after challenge all survivors were euthanized. The significance of the difference in mortality rates among the different groups was determined using a $G^2$ likelihood ratio test (Dixon, W. J., et al., *BMDP Statistical Software Manual*, University of California Press, 1988, pp. 229–273.) The results are summarized in Table 1.

TABLE 1

Protective Capacity of OmlA Against Challenge with *Actinobacillus pleuropneumoniae* serotype 1.

| GROUP | MORTALITY | | | CLINICAL SCORE | | |
| --- | --- | --- | --- | --- | --- | --- |
| | Day 1 | Day 2 | Day 3 | Day 1 | Day 2 | Day 3 |
| Placebo | 0/7 | 7/7 | 7/7 | 2.86 | 3.00 | — |
| OmlA-1 µg | 0/7 | 0/7 | 0/7 | 1.21 | 1.00 | 0.93 |
| OmlA-25 µg | 0/7 | 1/7 | 1/7 | 1.14 | 0.86 | 0.58 |

Within 2 days of challenge, all of the pigs which received the placebo were dead while only 1 of the OmlA-vaccinates had died. Clinical signs of disease were significantly lower in the vaccinates on day 1 post-challenge, the only day on which a comparison could be made due to high mortality in the placebo group. Thus, the omlA gene product of *A. pleuropneumoniae* (serotype 1) is an effective immunogen for the prevention of porcine pleuropneumonia caused by *A. pleuropneumoniae*. Immunization of pigs with the recombinant OmlA protein induced a strong immune response and significantly lowered mortality. These results demonstrate that protection against *A. pleuropneumoniae* serotype 1 can be achieved by immunization with a single protein antigen. Since the recombinant protein used for the vaccination trial was produced as an aggregate in *E. coli*, the lipid modification does not appear to be necessary for the induction of a protective immune response.

Example 6

The Protective Capacity of Sterotype 5 OmlA Recombinant Protein

OmlA protein was prepared from HB101/pSR213/E25 and formulated with Emulsigen Plus as described in Example 5 so that each 2 ml dose contained 25 µg of protein. Pigs were vaccinated, boosted and challenged with *A. pleuropneumoniae* serotype 5 strain AP213 as described in Example 5. The results shown in Table 2 indicate that vaccination with OmlA from serotype 5 reduced morbidity, mortality and lung damage associated with *Actinobacillus pleuropneumoniae* infection. It is predicted that vaccination with both serotype I and serotype 5 OmlA proteins would protect pigs against infection with all *A. pleuropneumoniae* serotypes, with the possible exception of serotype 11.

TABLE 2

Protective Capacity of OmlA Against Challenge with *Actinobacillus pleuropneumoniae* serotype 5.

| GROUP | MORTALITY | MEAN BODY TEMP. (°C.) | | | MEAN CLINICAL SCORE | | | LUNG SCORE |
|---|---|---|---|---|---|---|---|---|
| | | Day 1 | Day 2 | Day 3 | Day 1 | Day 2 | Day 3 | |
| Placebo | 3/3 | 40.87 | 40.40 | 41.00 | 1.33 | 1.58 | 2.13 | O |
| OmlA | 0/4 | 39.67 | 39.65 | 39.73 | 0.25 | 0.44 | 0.31 | ND |

Thus, subunit vaccines for use against *A. pleuropneumoniae* are disclosed, as are methods of making and using the same. Although preferred embodiments of the subject invention have been described in some detail, it is understood that obvious variations can be made without departing from the spirit and the scope of the invention as defined by the appended claims.

We claim:

1. A purified, *Actinobacillus pleuropneumoniae* outer membrane protein, wherein the protein is an immunogenic serotype 1 *Actinobacillus pleuropneumoniae* outer membrane lipoprotein A comprising an amino acid sequence as depicted in FIG. 1 (SEQ ID NO: 1).

2. A purified, *Actinobacillus pleuropneumoniae* outer membrane protein, wherein the protein is an immunogenic serotype 5 *Actinobacillus pleuropneumoniae* outer membrane lipoprotein A comprising an amino acid sequence as depicted in FIG. 2 (SEQ ID NO: 2).

3. A vaccine composition comprising a pharmaceutically acceptable vehicle and an immunogenic serotype 1 *Actinobacillus pleuropneumoniae* outer membrane lipoprotein A comprising an amino acid sequence as depicted in FIG. 1 (SEQ ID NO: 1).

4. The vaccine composition of claim 3 further comprising an adjuvant.

5. A method of treating or preventing an *Actinobacillus pleuropneumoniae* infection in a vertebrate subject comprising administering to said subject a therapeutically effective amount of a vaccine composition according to claim 3.

6. A method of treating or preventing an *Actinobacillus pleuropneumoniae* infection in a vertebrate subject comprising administering to said subject a therapeutically effective amount of a vaccine composition according to claim 4.

7. A vaccine composition comprising a pharmaceutically acceptable vehicle and an immunogenic serotype 5 *Actinobacillus pleuropneumoniae* outer membrane lipoprotein A comprising an amino acid sequence as depicted in FIG. 2 (SEQ ID NO: 2).

8. The vaccine composition of claim 7 further comprising an adjuvant.

9. A method of treating or preventing an *Actinobacillus pleuropneumoniae* infection in a vertebrate subject comprising administering to said subject a therapeutically effective amount of a vaccine composition according to claim 8.

10. A method of treating or preventing an *Actinobacillus pleuropneumoniae* infection in a vertebrate subject comprising administering to said subject a therapeutically effective amount of a vaccine composition according to claim 7.

11. A vaccine composition comprising:
    (a) a pharmaceutically acceptable vehicle;
    (b) an immunogenic serotype 1 *Actinobacillus pleuropneumoniae* outer membrane lipoprotein A comprising an amino acid sequence as depicted in FIG. 1 (SEQ ID NO: 1); and
    (c) an immunogenic serotype 5 *Actinobacillus pleuropneumoniae* outer membrane lipoprotein A comprising an amino acid sequence as depicted in FIG. 2 (SEQ ID NO: 2).

12. The vaccine composition of claim 11 further comprising an adjuvant.

13. A method of treating or preventing an *Actinobacillus pleuropneumoniae* infection in a vertebrate subject comprising administering to said subject a therapeutically effective amount of a vaccine composition according to claim 12.

14. A method of treating or preventing an *Actinobacillus pleuropneumoniae* infection in a vertebrate subject comprising administering to said subject a therapeutically effective amount of a vaccine composition according to claim 11.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1340 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 158..1252

( x i ) SEQUENCE DESCRIPTION: SEQ ID NO:1:

```
GATCGGCTTT  TACAGCGATT  GCAGAATGAT  TGAATTGTAA  ACTTTAGAGC  TTTATATTTT     60
GTTTAATGGT  ATTATATTTA  CTTATATTTA  TGATTCTTAG  TTTTTATTGT  AAATTAAAGT    120
GTTTATTTAT  TGTATTTTAA  GTATAAGGAA  TTTTTTAATG  AATATTGCAA  CAAAATTAAT    180
GGCTAGCTTA  GTCGCTAGTG  TAGTGCTTAC  CGCATGTAGT  GGCGGCGGCT  CATCGGGTTC    240
ATCGTCTAAA  CCAAATTCGG  AACTTACACC  TAAGGTTGAT  ATGTCCGCAC  CAAAAGCGGA    300
GCAGCCAAAA  AAAGAGGAAG  TTCCACAAGC  GGATAATTCG  AAAGCGGAAG  AACCAAAAGA    360
GATGGCTCCG  CAAGTAGATA  GCCCGAAAGC  GGAAGAACCA  AAAAATATGG  CTCCACAAAT    420
GGGTAATCCA  AAACTAAATG  ACCCACAAGT  AATGGCTCCG  AAAATGGATA  ATCCGCAAAA    480
AGATGCCCCA  AAAGGAGAAG  AACTAAGTAA  GGATAAAAGT  AATGCGGAAA  TTCTTAAGGA    540
ATTAGGGGTT  AAGGATATTA  ATTCAGGTAT  CATTAATAAT  GCTGATGTAG  TTCTGAATTT    600
AAAAATAGAT  GAAAAGATC   ACATTACAGT  CGTATTAGAT  AAGGGTAAGA  TTAATCGTAA    660
TCATCTAAAA  GTAACTAATA  CAATTTCTGC  TCAAGACATT  AAAACCTTAA  AAGATTCTTC    720
AGGCAAATTG  TTGGGTTACT  ATGGATATAT  GCAGTTAAAT  CAAGTTCGAC  AAGATGAAAA    780
TTATAGCGAT  GAAAAAGTTA  GTTTGAATGA  ATATTATTTA  TTATCAATGA  ACGATGCCGA    840
TAAAATACGT  CCGACTAAAT  CTATATCATA  TAAGGGAGAC  ATGTTTTATA  GTTACAAAGA    900
TGTAGGAAAT  CAGAAATTAA  AGGCTTCTGT  AGAAGCTTCT  TATGATGATG  TAACAAAAAA    960
AGTATCAATG  AAAGTATTTG  GTGAGAATAA  TGATTACTGG  AAATTAGGTG  AGTTTGGTAG   1020
AACTAATTTA  TTAGAAAATC  AAGTGACTGG  AGCAAAAGTT  GGCGAAGATG  GTACCATTAT   1080
AAATGGAACT  TTATATTCTA  AAATAGATAA  TTTTCCTTTA  AAACTAACTC  CTGACGCAAA   1140
CTTCTCTGGG  GGTATTTTCG  GTAAAAATGG  CGAAGTATTA  GCCGGAAGTG  CTATTAGTGA   1200
AAAATGGCAA  GGCGTAATCG  GTGCTACGGC  AACCACAAAA  GAAGATAAAA  AATAAACGCT   1260
```

```
TTGCTAACTA AACCAAAAGT TATCCTTCGG GATAGCTTTT TTACTTTTTA ATCAGACCTA    1320

ATAGTGCATC GGTAAAAGAT                                                1340
```

( 2 ) INFORMATION FOR SEQ ID NO:2:

( i ) SEQUENCE CHARACTERISTICS:
        ( A ) LENGTH: 2398 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 293..1393

( x i ) SEQUENCE DESCRIPTION: SEQ ID NO:2:

```
TCTAGAAAAT GCACTGACAA AATTAGGACT TCAGTGCGT GCCTATCATA GGATTTAAA      60

AGTTTCCCGC ACAATTGCCG ATTTGGCGAA CGAACCGAAT ATTCAACAAA TCCATCTTGC   120

CGAAGCGTTA GGTTATCGAG CGATGGATCG GCTTTTGCAG AGGTTGCAGA ACGATTAAAT   180

TGTAAACTTT AGAGCTTTAT ATTTGTTTG ATGGTATTAT ATTTATGATT TTTAGTTTTT    240

ATTGTAAATT AAAGTGTTTA TTATTGTAT TTAAGTATA AGGAATTTTT TAATGAATAT     300

TGCAACAAAA TTAATAGCCG GTTTAGTCGC AGGTTTAGTG CTTACCGCAT GTAGTGGCGG   360

CGGCTCATCG GGTTCATCGC CTAAACCAAA TTCGGAATCT ACGCCTAAGG TTGATATGTC   420

CGCACCAAAA GCGGAGCAGC CAAAAAAGA GGAAGCTCCG CAAGCGGATA GCCCGAAAGC    480

AGAAAAACCA AAAAGTATTG CTCCACTGAT GATGGAAAAC CCAAAAGTAG AGAAACAGAA   540

AGAAAATAAC CTACAAGAGA AAAGTCCAAA GGCAGACGAA CCGCAAGTAA TGGATCCAAA   600

ATTAGGTGCT CCACAAAAAG ATGATCAGAA GTTAGAAGAA CCTAAGAATA AAGTAATGC    660

GGAAATTCTT AAGGAATTAG GGATTAAGGA TATTACTTCA GGGACAATTA GTATTTCCGA   720

TATTGAATTG AATCTACAAT TAGATAGCAA TGATAATGTG AAAATATCTT TGTTAAATGA   780

GAATTTAATG CGTGATAATT TAACGATTAA TAATAAGATT GCAGGTTCGG ATATTAGAAC   840

GTTAAAAGAT TCTTCAGGTA GATTGTTAGG TTATTATGGT TATGTGCAAT TGAATCAAGT   900

TACACAAGAC TCTCGTGACC CAGATAATTA TAAGCATCAG TTTGAAAATC ATTATTTACT   960

GTCTATGAAT GATGCTGAGA AATATTACC AGAAAAGTCG TTAGAATATA AAGGTAGTAT   1020

GATTTACGGA TATAATACTT CTGGAAATGA AAAGCTTACT GCAGAAGTGA ATGCTAAATA  1080

TGATAGTTCA ACTAAAAAAT TATCAATGAA AGTATATGAT AATGATCGTT ATTGGAAATT  1140

AGGCGAAGTA ATGAGTAACA ATGTTAGATT ACCAGAAGAA AAAGTTGATG GTGTGAAAGT  1200

TGATTCTGAC GGAACAATTA ATGCTCGTTT ATATTTAAGC ACTGAAGAAC CATTAAAATT  1260

AACCCCTGAC GCCAATTTCT CCGGTGGTAT TTTTGGGAAA AACGGTGAAG TACTGGCAGG  1320

AAAAGCGGAA AGCATTAAGG GAGAATGGCA AGGCGTAATC GGTGCTACGG CAACAACAAA  1380

AGAAGATAAA AATAACGCT TTGCTTACCA AACTAAAGC TATCCTTCGG GATAGCTTTT   1440

TTACTTTTTA ATCAGTGCCA ATAGTGCATC GGTAAAAGAT TCCGGGTTTT CATAATGTGC   1500

GTTATGTCCG GCATTAGGAA TAAGCTGATG ATGAAGTTTA TTATCGGAGA CGATTTTCT   1560

AAATTTCCGA TCATATTCGC CGATCAAAAA AGTGATAGTC TGCCGAGCTT CGGAGAGCTG   1620

CGGTAAAAAA TAAGGTTGCT TTGCAAGACT AGTCGCTTCA AGCATAGCCG CAACAACTGA  1680

TCCGTTATTG TTTTGCGCCG AAAAACGATT AAATTTGGAC CGCTTGTGTT GGTCTAAATT  1740

GGCAAAAACG GCTTGTTGAT ACCAATCATT TAATACTTTC ACTATCGGTT CGTTACGGAA  1800

ACGTTTCGCC CATTGATGGT CGTTTTGCCA ACGAGCTTGG CGTTCCTCAT CTGTTGCTAA  1860
```

```
GCCGATGTTC  GCTCCTTCAA  GAATCGTATG  TTTTAGCTGA  GGATTATTGG  CATTGAGCGC   1920

ATAGTCAACG  CTAAACGCCC  GCCTAACGAA  TAGCCGACCA  AATAAAAAGG  CTGATTGCCG   1980

ATATAATGCA  GAACGGTTTG  ATGAATCAAT  TCTCTCGTGT  GGGAAAAGCC  GTAGCAGGGG   2040

ATATGTTCGC  TTGCCGCCAT  GCAGAGGAAG  GTCAATGGTA  AGCGGTCGAA  TTTGCGGAAA   2100

ANNNNNCTAG  CACCGCTTGC  CAAATCTTGT  TGCGAACCGA  GTAAACCGTG  CAGGAAAAA    2160

CCACCGGCAT  ACCCGTTTCA  CGATGCCATG  TTGCGTGGAG  CATTAGGCAA  TTTCCGCTTG   2220

TGAGATTTGT  TTAACTAAGG  ATTTGTAAAG  ATTGCTACCG  TCTTGATCGT  TCACTTTAAT   2280

TTCAACGCAT  AGTCACGCCT  TTACGTCCGT  AAGCGAGTTT  CAGTTTCGCT  TTCAGATCGG   2340

CCCAAGTAAA  CGGACGGATA  TATTCAATGC  CGAATATGGT  CGCAATCGGT  GCGAATTC    2398
```